United States Patent
Sekiya et al.

(10) Patent No.: US 6,694,728 B2
(45) Date of Patent: Feb. 24, 2004

(54) EXHAUST GAS DILUTION APPARATUS

(75) Inventors: Mitsunobu Sekiya, Kanagawa-ken (JP);
Susumu Fukushima, Kanagawa-ken (JP); Yoshihiro Yoshimura, Kanagawa-ken (JP); Tadashi Ikeda, Kanagawa-ken (JP)

(73) Assignee: Ono Sokki Co., Ltd., Yokohama (JP)

( * ) Notice: Subject to any disclaimer, the term of this patent is extended or adjusted under 35 U.S.C. 154(b) by 116 days.

(21) Appl. No.: 09/738,843

(22) Filed: Dec. 18, 2000

(65) Prior Publication Data

US 2001/0017031 A1 Aug. 30, 2001

(30) Foreign Application Priority Data

Dec. 28, 1999 (JP) .............................. 11-372428
Oct. 30, 2000 (JP) ........................ 2000-329943

(51) Int. Cl.[7] .............................. F01N 7/00
(52) U.S. Cl. .............................. 60/324; 60/274; 60/287; 60/291; 60/317; 73/118.1; 73/23.31; 73/23.32; 73/863.32; 73/863.41
(58) Field of Search ..................... 60/324, 274, 287, 60/288, 289, 291, 292, 293, 307, 316, 317, 318, 319; 73/118.1, 23.31, 23.32, 863.02, 863.03, 863.41, 863.32, 863.58, 863.81, 863.83

(56) References Cited

U.S. PATENT DOCUMENTS 5,090,258 A * 2/1992 Yamasaki et al. ......... 73/863.03
6,062,092 A * 5/2000 Weaver .................... 73/863.03
6,382,014 B1 * 5/2002 Breton ...................... 73/23.31
6,405,577 B2 * 6/2002 Hanashiro et al. ......... 73/23.31
6,435,019 B1 * 8/2002 Vojtisek-Lom ............. 73/118.1
6,470,732 B1 * 10/2002 Breton ...................... 73/23.31

FOREIGN PATENT DOCUMENTS

JP            09-325102           12/1997

OTHER PUBLICATIONS

Yoshinaka Takeda, et al., Society of Automotive Engineers of Japan Inc., Measurement of Diesel Particulate Using Mult–Tube Type Mini–Dilution Tunnel, 1990 JSAE Autumn Convention Proceedings 902 vol. 2, Oct. 17, 1990, pp. 2.49–2.52.

* cited by examiner

Primary Examiner—Binh Tran (57) ABSTRACT

An exhaust gas dilution apparatus 10-2 is the same form multi-venturi type comprising a rectifier 11, divider 12, exhaust chamber 14, dilution tunnel 15, and a divider pipes 13t on the dilution side of a tunnel 15 side. All divider pipes 13 are provided with a venturi 21 having the same performance inserted in the same position, to measure the flow rate in the dilution tunnel and the flow rate on the exhaust pipe side. The opening of the shutter 19 provided in the exit of the exhaust chamber 14 is controlled so that the two flow rates are equivalent.

20 Claims, 10 Drawing Sheets

▭ 21c VENTURI WITH A PRESSURE PORT

▱ 21cd DUMMY VENTURI WITH THE SAME A CONFIGURATION WITH THE ABOVE VENTURI, BUT WITHOUT A PRESSURE PORT

EXHAUST GAS DILUTION APPARATUS

BACKGROUND OF THE INVENTION

1. Field of the Invention

The present invention relates to an exhaust gas dilution apparatus used for measuring particulate emissions discharged from diesel engines and the like.

2. Description of the Background Art

A mini-tunnel system is given as a conventional exhaust gas dilution apparatus. According to this system, part of the exhaust gas from a diesel engine, for example, is removed and mixed with air in a dilution tunnel to produce and measure particulate emissions. It is important for this type of dilution apparatus to constantly segregate a certain proportion of the exhaust gas and to introduce such segregated gas into the dilution tunnel. An axisymmetric flow division system (Japanese Patent Application Laid-open No. 9-325102, etc.) has been proposed for this purpose.

Figure 10:
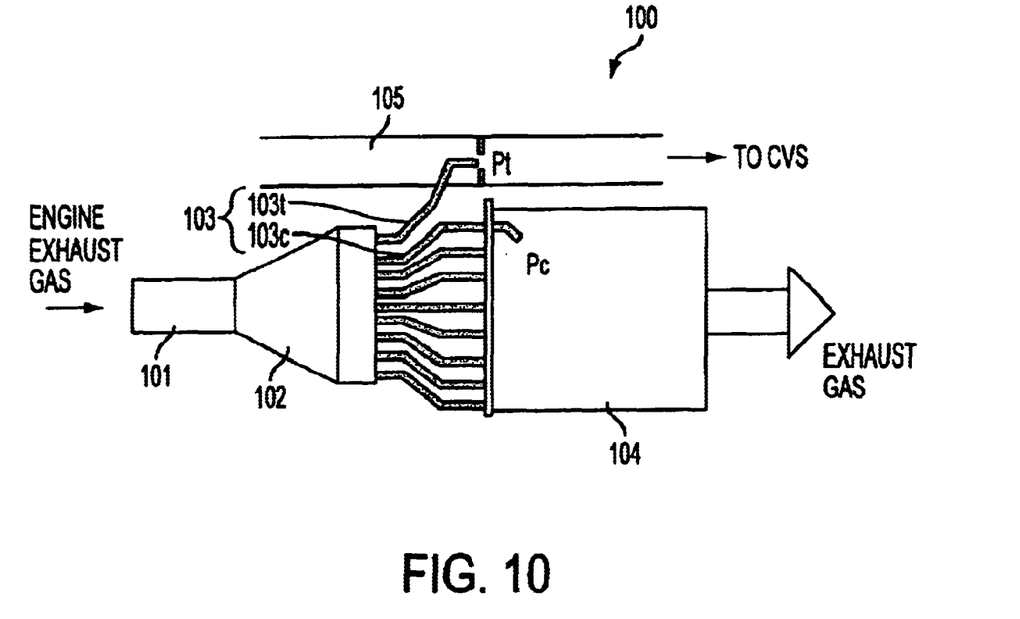
FIG. 10 is a schematic drawing showing an example of a conventional exhaust gas dilution apparatus of the axisymmetric flow division system.

FIG. 10 is a schematic drawing showing an example of a conventional exhaust gas dilution apparatus of this axisymmetric flow division system. This exhaust gas dilution apparatus 100 has a rectifier 101, a divider 102, a surge tank 104, a dilution tunnel 105, and the like.

The rectifier 101 adjusts the flow of exhaust gas from the engine exhaust pipe and introduces the gas into the divider 102.

The divider 102 divides the introduced exhaust gas into a plurality of flows by means of divider pipes 103 and extracts part of the gas to outside. This divider 102 is provided with a plurality of divider pipes 103 having the same length and diameter. Exhaust gas introduced into the divider 102 is divided by flowing into these divider pipes 103. A surge tank 104 is an exhaust chamber installed at the end of the divider 102 to recombine the gas flows divided by the divider 102 and discharge the combined gas.

An introduction pipe (a divider pipe on the dilution tunnel side) $103t$ is one of the divider pipes 103, which is folded outwardly from the divider 102 and extends to the dilution tunnel 105. Gas flowing into the introduction pipe $103t$ is led to, and discharged into the dilution tunnel 105. The dilution tunnel 105 is an air duct for diluting the exhaust gas introduced by the introduction pipe $103t$.

Because this system can divide the exhaust gas in a specified ratio according to the physical form of the divider 102, this type of exhaust gas dilution apparatus can divide gas more accurately than other conventional method such as a twin venturi type or multi-pipe type.

The aforementioned exhaust gas dilution apparatus shown in FIG. 10, however, cannot accurately divide the exhaust gas when the pressure Pc in the surge tank (exhaust chamber) 104 and the pressure Pt in the dilution tunnel 105 are not equivalent.

An object of the present invention is to overcome the above problems and to provide an exhaust gas dilution apparatus which can accurately divide the exhaust gas.

SUMMARY OF THE INVENTION

In order to attain the above object, a first invention provides an exhaust gas dilution apparatus equipped with a divider which divides exhaust gas introduced therein into a plurality of flows, extracts a portion of the gas to a dilution tunnel, and discharges the remaining portion to an exhaust chamber, wherein the exhaust gas dilution apparatus is characterized by comprising a first pressure detection means to detect the pressure in the dilution tunnel, a second pressure detection means to detect the pressure in the exhaust chamber, an exhaust adjustment means to adjust the exhaust gas in the exhaust chamber, and a control means to control the exhaust adjustment means so that the output of the first pressure detection means and the output of the second pressure detection means may become equivalent.

A second invention comprises an exhaust gas dilution apparatus equipped with a first divider which divides exhaust gas introduced therein into a plurality of flows and has a first divider pipe for extracting a portion of the gas into a dilution tunnel and a second divider pipe to discharge the remaining portion to an exhaust chamber, wherein the exhaust gas dilution apparatus is characterized by comprising a first and second flow rate measuring means having equivalent performance, provided in an equivalent position respectively in the first and second divider pipes, an exhaust adjustment means for adjusting exhaust from the exhaust chamber, and a control means to control the exhaust adjustment means so that the flow rate on the dilution tunnel side measured by the first flow rate measuring means and the flow rate on the exhaust pipe side measured by the second flow rate measuring means may become equivalent.

A third invention is the exhaust gas dilution apparatus having the same constitution as the exhaust gas dilution apparatus of the second invention, provided that the second flow rate measuring means comprises a plurality of venturis, one provided in each of the second dividers, a plurality of pressure difference detectors for measuring the pressure difference between the high pressure side and the low pressure side of each venturi, and an averaging circuit which averages the electric signals detected by the pressure difference detectors.

A fourth invention is an exhaust gas dilution apparatus having the same constitution as that of the second invention, provided that the second flow rate measuring means comprises a plurality of venturis for measurement, provided in representative dividers selected from the plurality of second dividers, and dummy venturis which are provided in the plurality of second dividers, excluding the dividers for which the venturis for measurement are provided, and have a throttle with the same configuration as that provided in the venturis for measurement.

A fifth invention is an exhaust gas dilution apparatus having the same constitution as that of the second invention, provided that the second flow rate measuring means comprises a plurality of venturis, one provided in each of the second dividers, and one pressure difference detector for measuring the pressure difference between the high pressure side and the low pressure side in combined pressure introduction pipes on the high pressure side and the low pressure side, which are formed by respectively combining the pressure introduction pipes of the venturis on the high pressure side and on the low pressure side.

A sixth invention provides an exhaust gas dilution apparatus equipped with a divider which divides exhaust gas introduced therein into a plurality of flows and has a first divider pipe for extracting a portion of the gas into a dilution tunnel and a second divider pipe for exhausting the remaining portion into an exhaust chamber, wherein the exhaust gas dilution apparatus is characterized by comprising first and second fluid throttling means having equivalent performance, provided in an equivalent position respectively in the first and second divider pipes, a high pressure side pressure difference detection means for detecting the pressure difference between the high pressure side of the first fluid throttling means and the high pressure side of the second fluid throttling means, a low pressure side pressure difference detection means for detecting the pressure difference between the low pressure side of the first fluid throttling means and the low pressure side of the second fluid throttling means, an exhaust adjustment means to adjust exhaust from the exhaust chamber, and a control means to control the exhaust adjustment means so that the pressure difference values detected by the low pressure side pressure difference detection means and the high pressure side pressure difference detection means may become equivalent and zero.

A seventh invention is an exhaust gas dilution apparatus having the same constitution as that of the sixth invention, provided that the high pressure side pressure difference detection means and the low pressure side pressure difference detection means are equipped with a cylinder, a free piston slidably inserted into the cylinder, and a piston position detecting means which detects the position of the free piston.

An eighth invention is an exhaust gas dilution apparatus having the same constitution as that of the first, second, or sixth invention, provided that the exhaust adjustment means is equipped with a suction which removes the gas in the exhaust chamber from downstream and an air introducing part which is provided between the exhaust chamber and the suction for introducing the atmospheric air.

A ninth invention is an exhaust gas dilution apparatus having the same constitution as that of the first invention, but further provided with a monitor means to continuously monitor the pressure values obtained by the first and/or second pressure detection means.

A tenth invention is an exhaust gas dilution apparatus having the same constitution as that of the first invention, but further comprising a result decision means which decides whether the pressure difference obtained by the first and second pressure detection means is within a previously specified range of deviation or above a previously specified correlation coefficient during a period of measurement, or decides, based on that result, whether the divider exhibits flow division performance within a permissible accuracy.

An eleventh invention is an exhaust gas dilution apparatus having the same constitution as that of the second invention, but further comprising a monitor means to continuously monitor the flow rate obtained by the first and/or second flow rate measuring means.

A twelfth invention is an exhaust gas dilution apparatus having the same constitution as that of the second invention, but further comprising a result decision means which decides whether the flow rate difference obtained by the first and second flow rate measuring means is within a previously specified range of deviation or above a previously specified correlation coefficient during a period of measurement, or decides, based on the results, whether the divider exhibits flow division performance in permissible accuracy.

A thirteenth invention is an exhaust gas dilution apparatus having the same constitution as that of the sixth invention, but further comprising a monitor means to continuously monitor the pressure difference obtained by the high pressure side pressure difference detection means and/or low pressure side pressure difference detection means.

A fourteenth invention is an exhaust gas dilution apparatus having the same constitution as that of the sixth invention, but further comprising a result decision means which decides whether the pressure difference obtained by the high pressure side and low pressure side pressure difference detection means is within a previously specified range of deviation or above a previously specified correlation coefficient during the period of measurement, or decides based on that result whether the divider exhibits flow division performance in permissible accuracy.

A fifteenth invention provides an exhaust gas dilution apparatus equipped with a divider which divides exhaust gas introduced therein into a plurality of flows and has a first divider pipe for extracting a portion of the gas into a dilution tunnel and a second divider pipe for exhausting the remaining portion to an exhaust chamber, wherein the exhaust gas dilution apparatus is characterized by comprising first and second flow rate measuring means having equivalent performance, provided in an equivalent position respectively in the first and second divider pipes, a fixed volume sampling means provided downstream of the dilution tunnel to cause the divided exhaust gas and dilution gas to flow at a constant rate and collect samples, a gas circulation means to recycle exhaust gas from the fixed volume sampling means to upstream of the divider during the time when the engine to be measured is not operating, and a correction means to correct the flow dividing precision of the divider based on the flow rate on the dilution tunnel side measured by the first flow rate measuring means and the flow rate on the exhaust pipe side measured by the second flow rate measuring means.

A sixteenth invention provides an exhaust gas dilution apparatus equipped with a divider which divides exhaust gas introduced therein into a plurality of flows and has a first divider pipe for extracting a portion of the gas into a dilution tunnel and a second divider pipe for exhausting the remaining portion to an exhaust chamber, wherein the exhaust gas dilution apparatus is characterized by comprising first and second fluid throttling means having equivalent performance, provided in an equivalent position respectively in the first and second divider pipes, a high pressure side pressure difference detection means for detecting the pressure difference between the high pressure side of the first fluid throttling means and the high pressure side of the second fluid throttling means, a low pressure side pressure difference detection means for detecting the pressure difference between the low pressure side of the first fluid throttling means and the low pressure side of the second fluid throttling means, a fixed volume sampling means provided downstream of the dilution tunnel to cause the divided exhaust gas and dilution gas to flow at a constant rate and collect samples, a gas circulation means to recycle exhaust gas from the fixed volume sampling means to upstream of the divider during the time when the engine to be measured is not operating, and a correction means to correct the flow dividing precision of the divider based on the pressure difference value detected by the high pressure side pressure difference detection means and the low pressure side pressure difference detection means.

A seventeenth invention provides an exhaust gas dilution apparatus equipped with a divider which divides exhaust gas introduced therein into a plurality of flows, extracts a portion of the gas to a dilution tunnel, and discharge the remaining portion to an exhaust chamber, wherein the exhaust gas dilution apparatus is characterized by comprising a fixed volume sampling means provided downstream of the dilution tunnel to cause the divided exhaust gas and dilution gas to flow at a constant rate and collect samples, and a gas circulation means to recycle exhaust gas from the fixed volume sampling means to upstream of the divider during the time when the engine to be measured is not operating.

DETAILED DESCRIPTION OF THE INVENTION AND PREFERRED EMBODIMENTS

The present invention will be described in more detail by way of preferred embodiments with reference to the attached drawings.

(First Embodiment)

Figure 1:
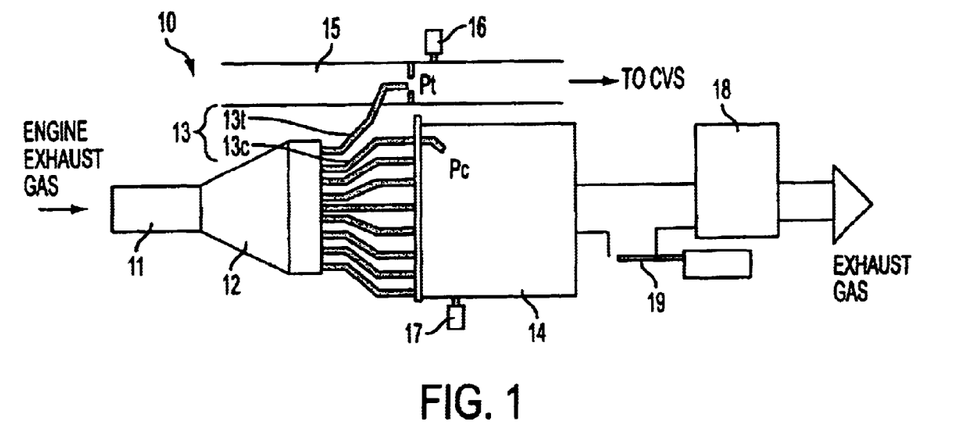
FIG. 1 is a drawing schematically showing a first embodiment of the exhaust gas dilution apparatus of the present invention.

FIG. 1 is a drawing schematically showing a first embodiment of the exhaust gas dilution apparatus of the present invention. In the embodiments described hereinafter, the parts having the same functions as those of the above-mentioned conventional embodiments are indicated by the same reference numerals or by adding common symbols after the numerals, and the drawings and descriptions for these parts will be omitted to the extent of avoiding duplication.

The exhaust gas dilution apparatus 10 of the first embodiment comprises a first pressure sensor 16 which detects the pressure in a dilution tunnel 15, a second pressure sensor 17 which detects the pressure inside an exhaust chamber 14, a blower 18 which removes the gas in the exhaust chamber 14 from downstream, and a shutter 19 which is provided between the exhaust chamber 14 and the blower 18 to introduces air from outside. Opening of the shutter 19 is controlled so that the pressure Pc in the exhaust chamber 14 and the pressure Pt in the dilution tunnel 15 may be equivalent.

In this first embodiment, the exhaust gas can be accurately divided because the pressure Pt in the dilution tunnel 15 and the pressure Pc in the exhaust chamber 14 are maintained equivalent.

(Second Embodiment)

Figure 2:
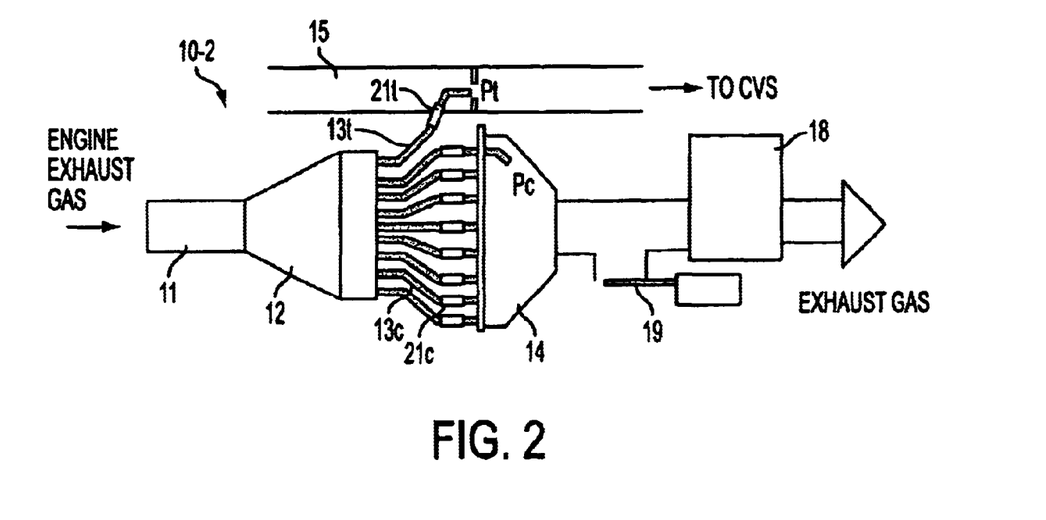
FIG. 2 is a drawing schematically showing a second embodiment of the exhaust gas dilution apparatus of the present invention.

FIG. 2 is a drawing schematically showing a second embodiment of the exhaust gas dilution apparatus of the present invention.

An exhaust gas dilution apparatus 10-2 of the second embodiment is of a multi-venturi type with all venturis having the same configuration. All divider pipes 13, including the divider pipe 13t on the side of a dilution tunnel 15, are equipped with a venturi 21 with equivalent performance at the same position for measuring the flow rate on the dilution tunnel side and the flow rate on the exhaust pipe side. Opening of a shutter 19 provided at the exit of an exhaust chamber 14 is controlled so that these flow rates may be equivalent.

The second embodiment has solved the following problems in the apparatus of the first embodiment.

(1) It is difficult to accurately detect the pressure in the dilution tunnel 15 of the first embodiment due to the structure inherent in the apparatus of the first embodiment such as the requirement for providing a blending orifice and the like.

(2) The pressure inside the exhaust chamber 14 of the first embodiment varies according to the measuring position because the pressure is measured at a point in a large volume of flowing gas.

(3) The speed of response for the pressure detection and pressure control is slow when measuring particulate emissions during a transient run.

Figure 3:
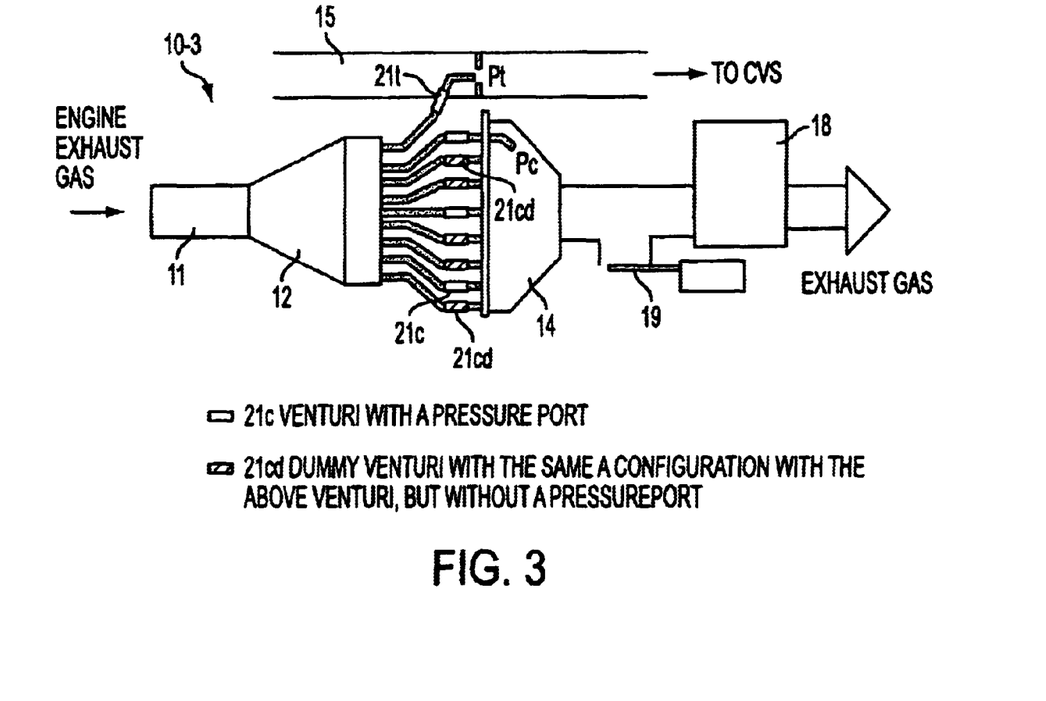
FIG. 3 is a drawing schematically showing a modified exhaust gas dilution apparatus of the second embodiment.

FIG. 3 is a drawing schematically showing a modified exhaust gas dilution apparatus of the second embodiment.

FIG. 2 describes an example wherein the flow rates in the venturis 21c on the exhaust pipe side are measured in all divider pipes 13c, whereas in an exhaust gas dilution apparatus 10-3 shown in FIG. 3, only some representative divider pipes 13c are used for measurement of the flow rate.

In this embodiment, a dummy venturi 21cd having a throttle with the same configuration (except for omission of a pressure detection opening) as the venturis 21c which are used for the measurement is installed in each divider pipe 13c in which the flow rate is not measured.

Figure 4A:
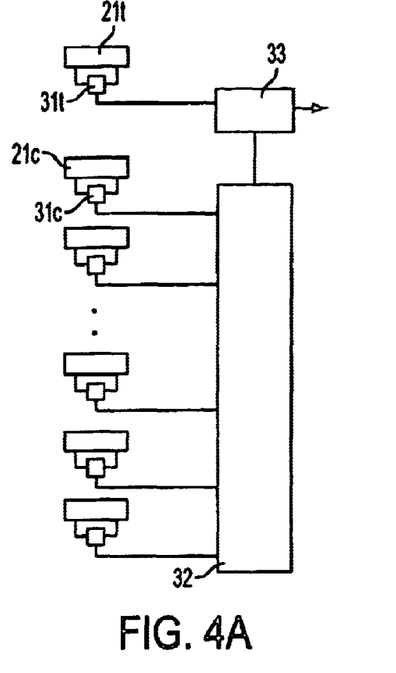
FIG. 4 is a drawing showing an averaging process for the exhaust gas dilution apparatus of the second embodiment.
Figure 4B:
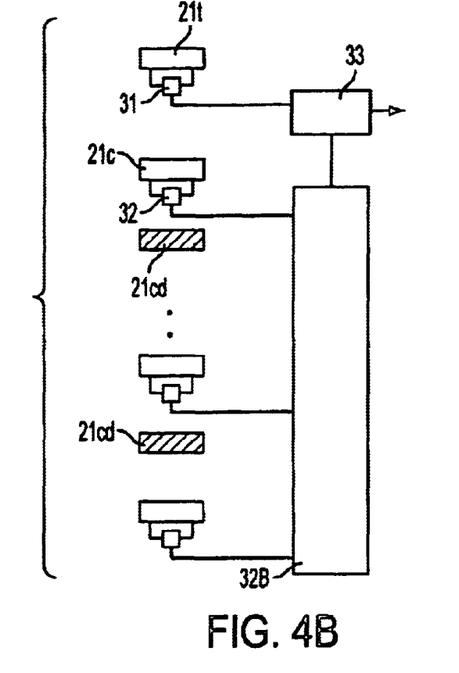

FIG. 4 is a drawing showing an averaging process for the exhaust gas dilution apparatus of the second embodiment.

In the embodiment shown in FIG. 2, the flow rates in a number of divider pipes which lead exhaust gas to the exhaust chamber side (hereinafter called "divider pipes on the discharged exhaust side") are measured by venturis 21c and detected as electric signals. The signal values are averaged and the resulting mean value is used for the control operation. Specifically, as shown in FIG. 4(A), the apparatus comprises a pressure difference detector 31t provided in the venturi 21t of the divider pipe on the dilution tunnel side, pressure difference detectors 31c provided in the venturis 21c of the divider pipes on the discharged exhaust side, an averaging circuit 32 which averages the values detected by the pressure difference detectors 31c, a comparison-control circuit 33 which compares the output of the pressure difference detector 31t and the output of the averaging circuit 32 and controls the opening of the shutter 19 so that the two pressure values may become equal, and the like.

FIG. 4(B) shows an averaging process for the apparatus shown in FIG. 3, and comprises an averaging circuit 32B which averages the detected values of pressure difference detectors 31c provided in venturis 21c, excluding dummy venturis 21cd, of the divider pipes on the discharged exhaust side.

Figure 5A:
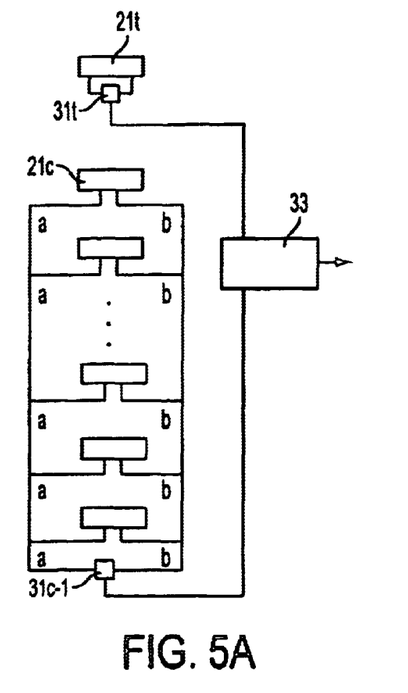
FIG. 5 is a drawing showing a modified averaging process for the exhaust gas dilution apparatus of the second embodiment.
Figure 5B:
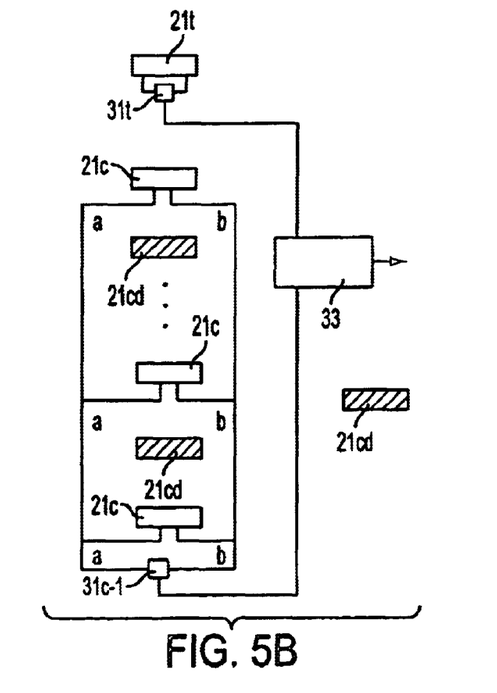

FIG. 5 is a drawing showing a modified averaging process for the exhaust gas dilution apparatus of the second embodiment.

The embodiment shown in FIG. 5(A) is designed so as to combine the pressure introduction pipes of the high pressure side a and the low pressure side b for the venturis 21c in divider pipes on the discharged exhaust side and introduce the combined gas to one pressure difference detector 31c-1.

FIG. 5(B) shows an averaging process used for the apparatus shown in FIG. 3. In this system, the pressure introduction pipes for venturis 21c, excluding dummy venturis 21cd, of the divider pipes on the discharged exhaust side are combined to introduce the combined exhaust gas to one pressure difference detector 31c-1.

Figure 6:
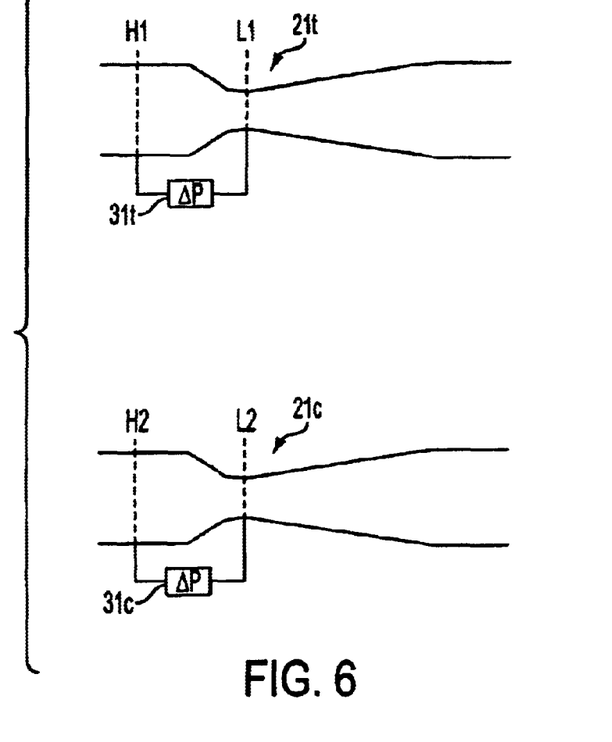
FIG. 6 is a drawing for illustrating a pressure difference detection method for venturis in the exhaust gas dilution apparatus of the second embodiment.

FIG. 6 is a drawing for illustrating a pressure difference detection method for venturis in the exhaust gas dilution apparatus of the second embodiment.

The pressure difference detector 31t detects the pressure difference (H1–L1), which is the difference between the pressure H1 on the high pressure side and the pressure L1 on the low pressure side of the venturi 21t for the divider pipe on the dilution tunnel side, and the pressure difference (H2–L2), which is the difference between the pressure H2 on the high pressure side and the pressure L2 on the low pressure side of the venturis 21c for the divider pipes on the discharged exhaust side, each as electric signals. The comparison-control circuit 33 controls the operation so that the equation (H1–L1)=(H2–L2) may be satisfied.

When detection is carried out using the system, a large measurement range is required for the pressure difference detectors 31t and 31c because the discharge quantity during engine idling differs greatly from the discharge quantity during full load running in this system.

Therefore, the pressure of each venturi used for the control was processed as shown in FIG. 6. It is also possible to use the system shown in FIG. 7.

Figure 7:
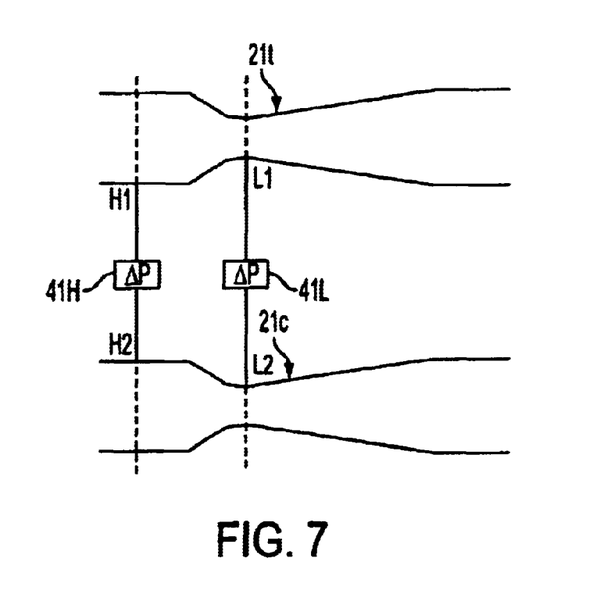
FIG. 7 is a drawing for illustrating another modified pressure difference detection method for the venturis in the exhaust gas dilution apparatus of the second embodiment.

FIG. 7 is a drawing for illustrating another modified pressure difference detection method for the venturis in the exhaust gas dilution apparatus of the second embodiment.

As described above, the difference between the pressure difference signal (H2–L2) obtained from the venturis of the divider pipes on the discharged exhaust side and the pressure difference signal (H1–L1) obtained from the venturi of the divider pipe on the dilution sample tube side, (H1–L1)–(H2–L2), is used for control.

Therefore, a pressure difference detector with a large detection range is disadvantageous in terms of control characteristics due to the problems with S/N and resolving capability.

For this reason, a pressure difference detector 41H on the high pressure side for detecting the pressure difference (H1–H2), which is the difference between the pressure H1 on the high pressure side of the venturi 21t for the divider pipe on the dilution tunnel side and the pressure H2 on the high pressure side of the venturis 21c for divider pipes on the discharged exhaust side, and a pressure difference detector 41L on the low pressure side for detecting the pressure difference (L1–L2), which is the difference between the pressure L1 on the low pressure side of the venturi 21t for the divider pipe on the dilution tunnel side and the pressure L2 on the low pressure side of the venturis 21c for divider pipes on the discharged exhaust side, are provided as shown in FIG. 7. The comparison-control circuit 33 controls the operation so that the equation (H1–H2)=(L1–L2)=0 may be satisfied.

Because both pressure differences become close to zero in the case of FIG. 7, a pressure difference detector 41 with a small range may be used, whereby the above problem can be solved.

For example, it is necessary to control a pressure of 0.1 kPa for a pressure range of 30 kPa using the pressure difference detector 31 in FIG. 6, whereas a pressure of 0.1 kPa may be controlled for a pressure range of 3 kPa if the pressure difference detector 41 shown FIG. 7 is used. This is about one digit improvement in resolution.

In addition, the method shown in FIG. 7 makes it possible to detect a pressure difference using a free piston 42 instead of the pressure difference detector 41.

Figure 8A:
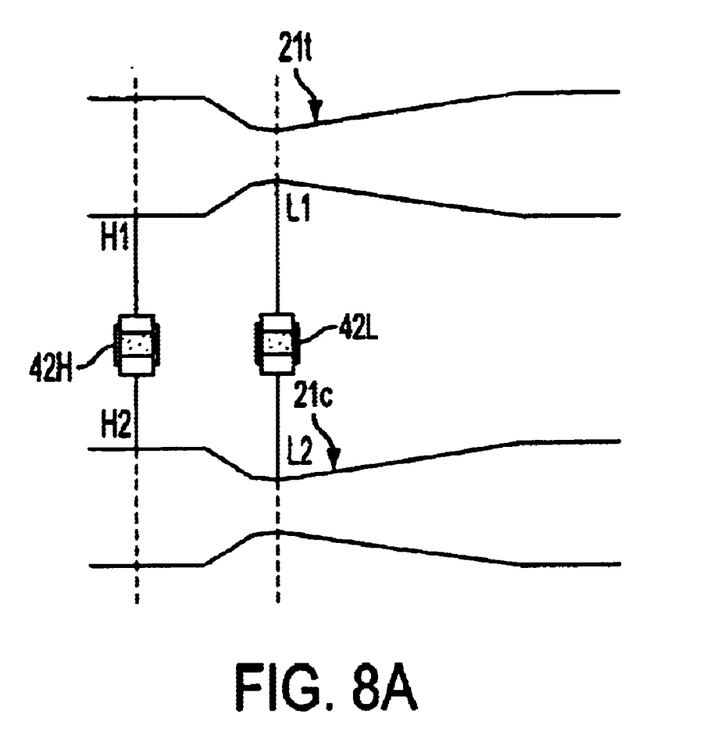
FIG. 8 is a drawing for illustrating a pressure difference detection method for the venturis in the exhaust gas dilution apparatus of the second embodiment using a free piston.
Figure 8B:
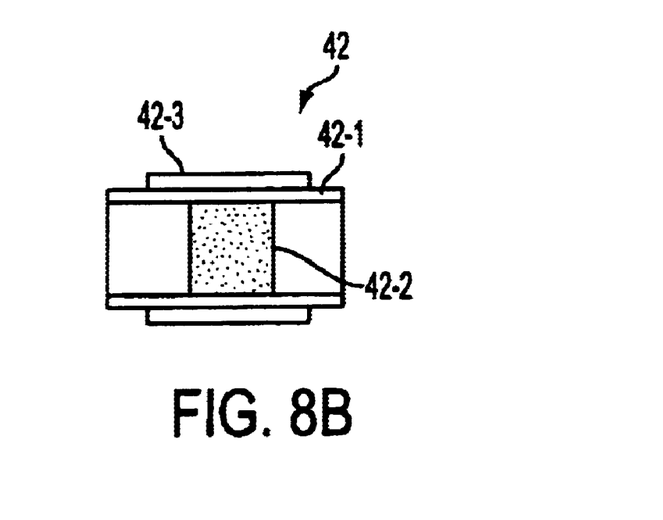

FIG. 8 is a drawing for illustrating a pressure difference detection method for the venturis in the exhaust gas dilution apparatus of the second embodiment using a free piston.

As shown in FIG. 8(A), a free piston-type pressure difference detector 42H for detecting the pressure difference (H1–H2), which is the difference between the pressure H1 on the high pressure side of the venturi 21t for the divider pipe on the dilution tunnel side and the pressure H2 on the high pressure side of the venturis 21c for divider pipes on the discharged exhaust side, and a free piston-type pressure difference detector 42L for detecting the pressure difference (L1–L2), which is the difference between the pressure L1 on the low pressure side of the venturi 21t for the divider pipe on the dilution tunnel side and the pressure L2 on the low pressure side of the venturis 21c for divider pipes on the discharged exhaust side, are provided. The comparison-control circuit 33 controls the operation so that the equation (H1–H2)=(L1–L2)=0 may be satisfied.

As shown in FIG. 8(B), the free piston-type pressure difference detector 42 is formed from a cylinder 42-1, a free piston 42-2 slidably inserted into the cylinder 42-1, and a piston position detecting means 42-3 which detects the position of the free piston 42-2.

Use of the free piston-type pressure difference detector 42 not only enables the pressure difference detection apparatus to withstand excessive pressure, but also contributes to reduction of costs.

Figure 9:
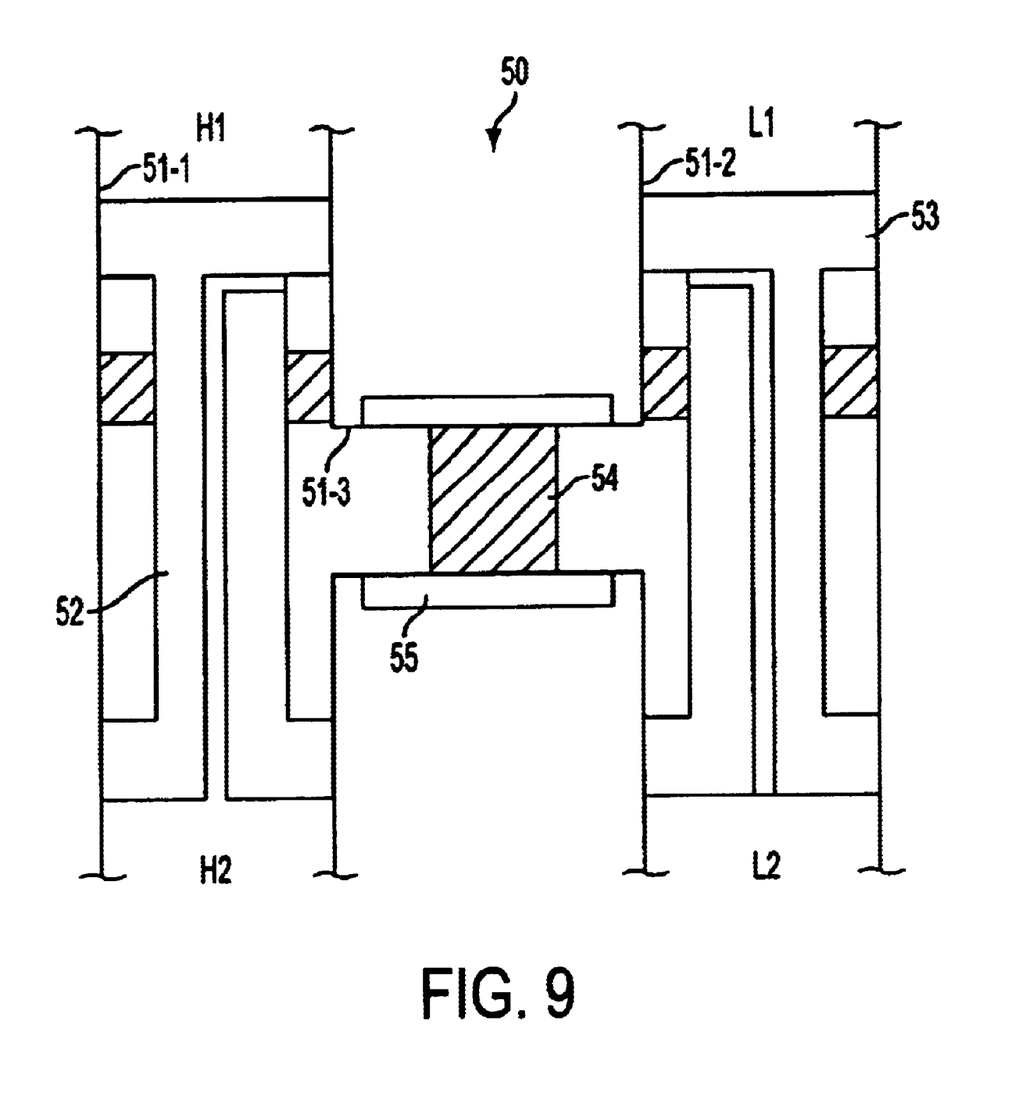
FIG. 9 is a drawing for illustrating a modified pressure difference detection method for the venturis in the exhaust gas dilution apparatus of the second embodiment using a free piston.

FIG. 9 is a drawing for illustrating a modified pressure difference detection method for the venturis in the exhaust gas dilution apparatus of the second embodiment using a free piston.

This pressure difference detector 50 is formed from an H-type cylinder 51 provided with a high pressure side introduction pipe 51-1, a low pressure side introduction pipe 51-2, and a connecting pipe 51-3 which connects these pipes; a free piston 52 inserted into the high pressure side introduction pipe 51-1, with the head sections connected to the high pressure side (H1) of the venturi 21t of the divider pipe on the dilution tunnel side and the high pressure side (H2) of the venturis 21c of divider pipes on the discharged exhaust side; a free piston 53 inserted into the low pressure side introduction pipe 51-2, with the head sections connected to the low pressure side (L1) of the venturi 21t of the divider pipe on the dilution tunnel side and the low pressure side (L2) of the venturis 21c of divider pipes on the discharged exhaust side; a free piston 54 inserted into the connecting pipe 51-3; and a piston position detecting means 55 which detects the position of the free piston 54.

This embodiment makes it possible to operate the system using only one piston position detecting means 55 (which is expensive equipment), thereby reducing costs.

(Third Embodiment)

Figure 11:
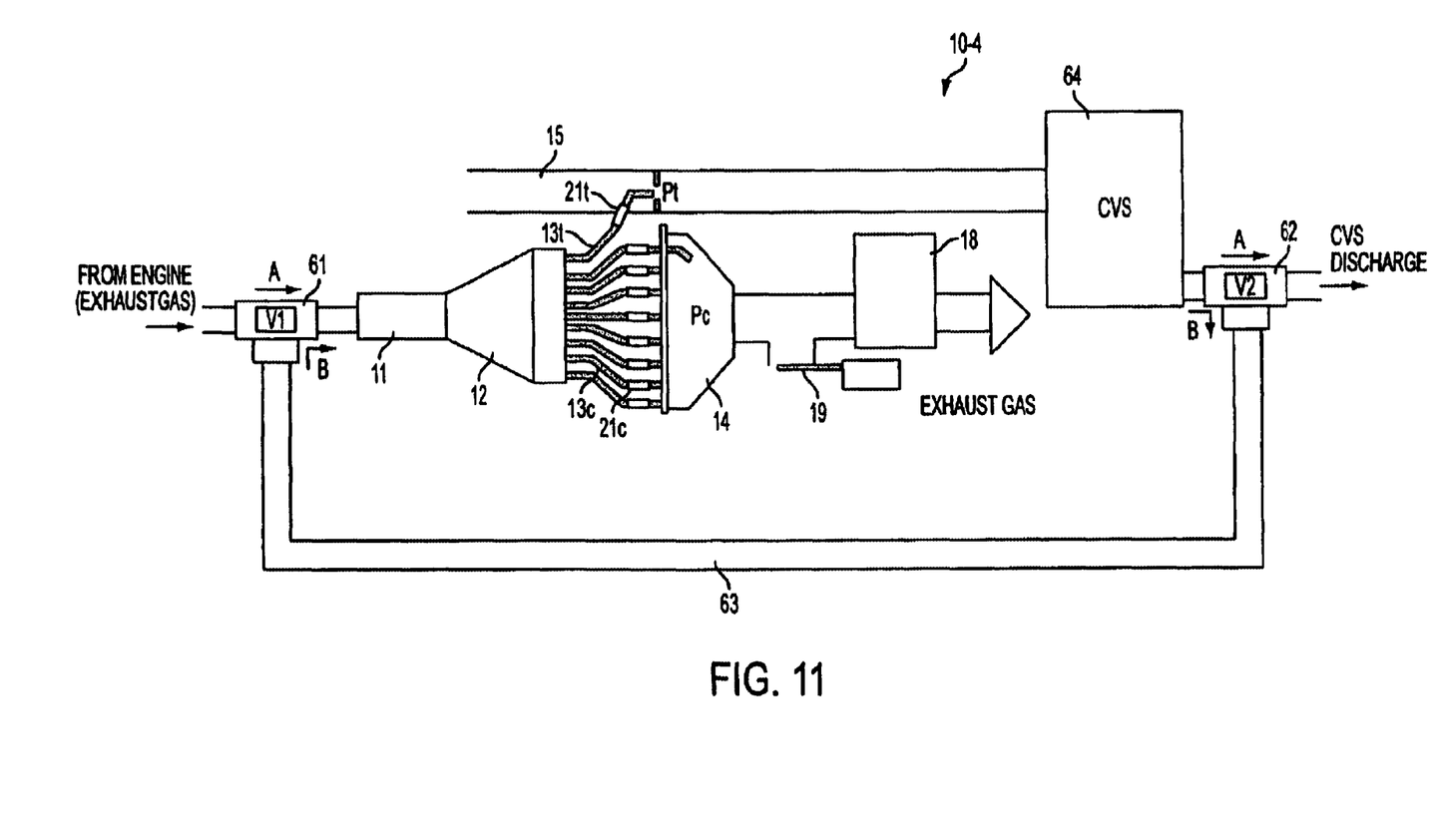
FIG. 11 is a drawing schematically showing a third embodiment of the exhaust gas dilution apparatus of the present invention.
Figure 12:
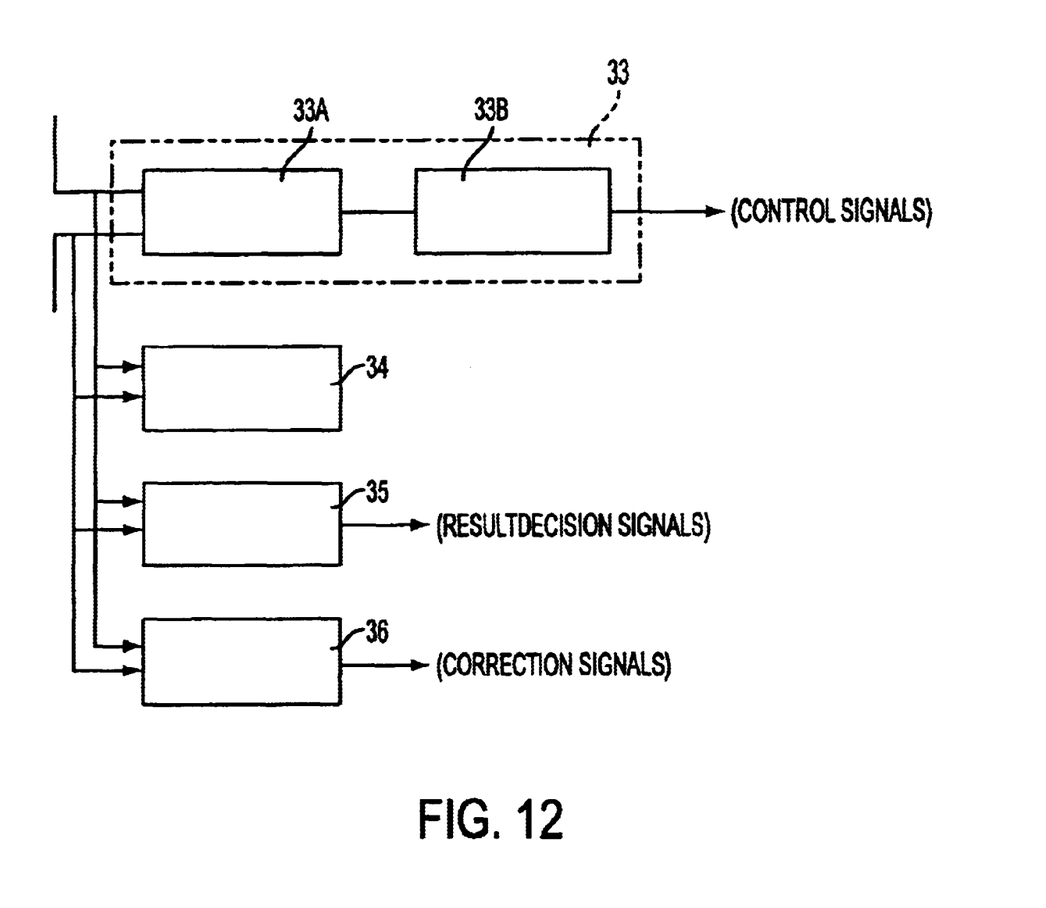
FIG. 12 is a block diagram showing the control system for the exhaust gas dilution apparatus of the third embodiment.
Figure 13A:
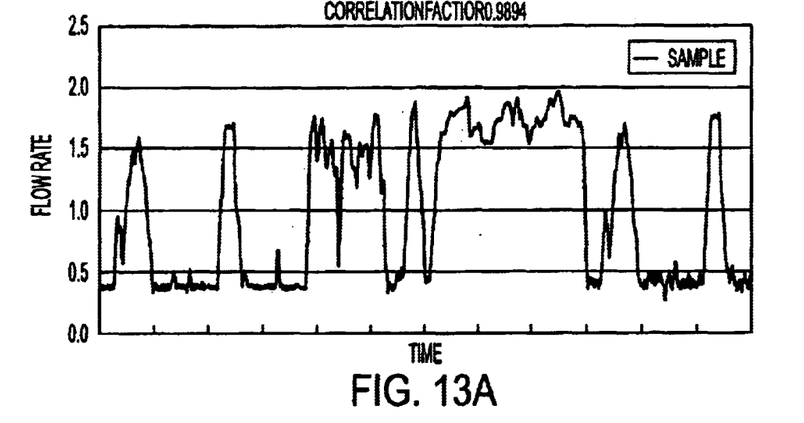
FIG. 13 is a drawing showing an example of monitor displays in the exhaust gas dilution apparatus of the third embodiment.
Figure 13B:
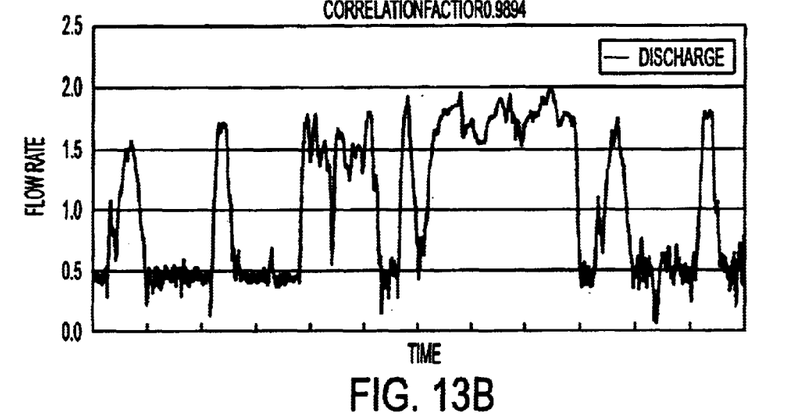
Figure 13C:
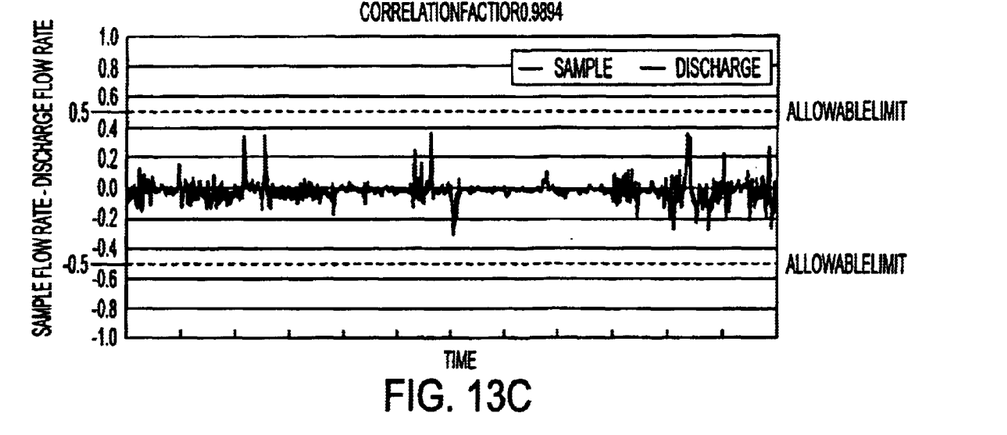

FIG. 11 schematically shows a third embodiment of the exhaust gas dilution apparatus of the present invention, FIG. 12 is a block diagram showing a control system for the exhaust gas dilution apparatus of the third embodiment, and FIG. 13 shows an example of a monitor display in the exhaust gas dilution apparatus of the third embodiment.

The exhaust gas dilution apparatus 10-4 of the third embodiment is almost the same as the exhaust gas dilution apparatus 10-2 of the second embodiment shown in FIG. 2 inasmuch as the basic structure of the dilution apparatus is concerned, except that the former is additionally provided with a monitor function, a result decision function for determining the flow dividing accuracy of the divider, and a correction function for correcting the flow dividing accuracy of the divider.

As shown in FIG. 11, this exhaust gas dilution apparatus 10-4 has a circulation means consisting of a three way valve 61 provided upstream of a rectifier 11 for switching the gas flow route, a three way valve 62 provided downstream of a CVS 64 for switching the gas flow route, a recycle tube 63 (circulation means) connecting the three way valves 61 and 62, and the like, in addition to the components provided in the exhaust gas dilution apparatus 10-2 of the second embodiment. The CVS64 is provided downstream of the dilution tunnel 15 and functions as a fixed volume sampler (a fixed volume sampling means) ensuring a flow of a fixed volume of gas.

As shown in FIG. 12, the control system is provided with a monitor 34 to which the output of a comparative circuit 33A of the control-comparative circuit 33 is connected, a decision circuit 35, and a correction circuit 36, in addition to the components shown in the block diagram of FIG. 4.

The monitor 34 is an apparatus for continuously monitoring the flow rates obtained from the venturi 21$t$ on the dilution tunnel side and the venturis 21$c$ in the divider pipes on the discharged exhaust side. The monitor 34 ensures confirmation of the flow dividing conditions by the divider 12 in particulate emissions sampling during measurement.

The decision circuit 35 continuously monitors the flow rates obtained from the venturi 21$t$ on the dilution tunnel side and the venturis 21$c$ in the divider pipes on the discharged exhaust side and judges whether the flow rate difference is within or outside a previously specified range of deviation, or determines whether the divider 12 exhibits flow division performance within permissible accuracy. The decision circuit 35 makes it possible to judge whether the measurement results are correct or not.

The correction circuit 36 is a circuit which creates correction signals to correct flow dividing precision of the divider 12.

Operation of the exhaust gas dilution apparatus 10-4 of the third embodiment will now be described.

During correction, the engine which is the measuring target is stopped and the three-way valves 61, 62 (V1, V2) are switched in the direction indicated by an arrow B to circulate the exhaust gas from the CVS 64 to upstream of the rectifier 11 through the return pipe 63.

At this time, the correction circuit 36 compares the flow rate indicated by the venturi 21$c$ installed in divider pipes 13$c$ discharging exhaust gas to the exhaust chamber 14 and the flow rate indicated by the venturi 21$t$ installed in the divider pipe 13$t$ discharging exhaust gas to the dilution tunnel 15 with a standard value of the dividers which has been previously determined, creates correction signals based on the results of the comparison, and corrects the flow dividing precision (the flow dividing ratio) of the divider 12.

Correction of the flow dividing precision of the divider 12 is important to maintain the measuring accuracy of the exhaust gas dilution apparatus of the present invention. When correcting the flow dividing precision in the conventional exhaust gas dilution apparatus in the state where piping has been arranged, the engine connected to the driving system is rotated by a motor to measure the amount of intake air by a flow meter and the divided flow rate on the dilution tunnel side. The flow dividing precision is corrected based on the results. In this case, an intake flow meter is necessary to know the total quantity of flow.

On the other hand, in the present embodiment the engine is stopped during the correction operation and the exhaust gas from the CVS 64 is returned to the rectifier 11 to correct the flow dividing precision based on the flow rate in the divider pipes 13$c$ discharging the exhaust to the exhaust chamber 14 and the flow rate in the divider pipe 13$t$ which extracts the exhaust into the dilution tunnel 15. In this instance, because the exhaust gas is discharged from the CVS 64 at a fixed, known flow rate, the flow dividing precision of the divider 12 can be determined without a flow meter to determine the total quantity of flow as in the conventional apparatus.

Although the embodiment shown in FIG. 11 is equipped with a shutter 19 to control the amount of air introduced so as to equalize the pressure inside the exhaust chamber 14 and the pressure inside the dilution tunnel 15, the flow dividing precision can be corrected in the same manner without such equipment.

Next, the three-way valves 61, 62 (V1, V2) are switched in the direction indicated by an arrow A during measurement. At this time, the monitor 34 displays the output from the pressure difference detector 31$t$ (FIG. 13($a$)) installed in the venturi 21$t$ on the dilution tunnel side in the FIG. 4, the output from the averaging circuit 32 (FIG. 13($b$)) determined by averaging the detection values from a plurality of pressure difference detectors 31$c$ installed in the venturis 21$c$ in the divider pipes on the discharged exhaust side, and the difference of the two outputs (FIG. 13 ($c$)).

In addition, the decision circuit 35 judges whether the difference between the two outputs is within a previously specified range of deviation or exceeds a previously specified correlation coefficient, or determines, based on that result, whether the divider 12 exhibits flow division performance within permissible accuracy. Based on the above result, the decision circuit decides whether the measured amount of particulate emissions is valid or invalid. In addition, it is possible for the measuring personnel to judge validity of the measured amount based on the numerical results such as a correlation coefficient and the like.

The present invention is not limited to the above-described embodiment and can be varied or modified in various ways. Such variations and modifications are within the scope of equivalency of the present invention.

For example, although the third embodiment was described as a modification of the second embodiment shown in FIG. 2 with the addition of the monitor 34, result decision circuit 35, and correction circuit 36, such an addition is also possible in other embodiments such as the first embodiment shown in FIG. 1 or the second embodiment shown in FIG. 3 and other figures.

As described above in detail, the present invention ensures accurate division of exhaust gas when the exhaust gas is to be divided into a plurality of flows to extract part thereof to a dilution tunnel.

Obviously, numerous modifications and variations of the present invention are possible in light of the above teachings. It is therefore to be understood that, within the scope of the appended claims, the invention may be practiced otherwise than as specifically described herein.

What is claimed is:

1. In an exhaust gas dilution apparatus equipped with a divider which divides exhaust gas introduced therein into a plurality of flows and has a first divider pipe for extracting a portion of the gas into a dilution tunnel and a second divider pipe for exhausting a remaining portion of the gas to an exhaust chamber, the exhaust gas dilution apparatus comprising:

first and second flow rate measuring means having equivalent performance, provided in an equivalent position respectively in the first and second divider pipes;

exhaust adjustment means for adjusting an exhaust from the exhaust chamber; and control means for controlling the exhaust adjustment means so that a flow rate of the dilution tunnel measured by the first flow rate measuring means and a flow rate of the exhaust pipe side measured by the second flow rate measuring means are equivalent.

2. The exhaust gas dilution apparatus according to claim 1, wherein the second flow rate measuring means comprises:

dividers, a plurality of venturis, one provided in each of the dividers, a plurality of pressure difference detectors for measuring a pressure difference between a high pressure side and a low pressure side of each venturi, and an averaging circuit which averages the electric signals detected by the pressure difference detectors.

3. The exhaust gas dilution apparatus according to claim 1, wherein the second flow rate measuring means comprises:

a plurality of dividers, a plurality of venturis for measurement in representative dividers selected from the plurality of dividers, and dummy venturis in the plurality of dividers, excluding the dividers for which the venturis for measurement are provided, and have a throttle with the same configuration as that provided in the plurality of venturis for measurement.

4. The exhaust gas dilution apparatus according to claim 1, wherein the second flow rate measuring means comprises:

dividers, pressure introduction pipes, a plurality of venturis, one provided in each of the dividers, and one pressure difference detector for measuring a pressure difference between a high pressure side and a low pressure side in combined pressure introduction pipes on the high pressure side and the low pressure side, which are formed by respectively combining the pressure introduction pipes of the plurality of venturis on the high pressure side and the low pressure side.

5. The exhaust gas dilution apparatus according to claim 1, further comprising:

monitor means for continuously monitoring the flow rates obtained by the first and/or second flow rate measuring means.

6. The exhaust gas dilution apparatus according to claim 1, further comprising:

result decision means for determining whether differences in the flow rates obtained by the first and second flow rate measuring means are within a previously specified range of deviation or above a previously specified correlation coefficient during a period of measurement and outputting results indicative thereof, or for determining based on the results, whether the divider exhibits flow division performance with permissible accuracy.

7. In an exhaust gas dilution apparatus equipped with a divider which divides exhaust gas introduced therein into a plurality of flows and has a first divider pipe for extracting a portion of the gas into a dilution tunnel and a second divider pipe for exhausting the remaining portion to an exhaust chamber, the exhaust gas dilution apparatus comprising:

first and second fluid throttling means having equivalent performance, provided in an equivalent position respectively in the first and second divider pipes;

high pressure side pressure difference detection means for detecting a first pressure difference between a high pressure side of the first fluid throttling means and a high pressure side of the second fluid throttling means;

low pressure side pressure difference detection means for detecting a second pressure difference between a low pressure side of the first fluid throttling means and a low pressure side of the second fluid throttling means;

exhaust adjustment means for adjusting an exhaust from the exhaust chamber; and control means for controlling the exhaust adjustment means so that the first and second pressure differences detected are equivalent and zero.

8. The exhaust gas dilution apparatus according to claim 7, wherein the high pressure side pressure difference detection means and the low pressure side pressure difference detection means each comprise a cylinder, a free piston slidably inserted into the cylinder, and a piston position detecting means for detecting a position of the free piston.

9. The exhaust gas dilution apparatus according to claim 7, further comprising:

monitor means for continuously monitoring the first and/or the second pressure differences obtained by the high pressure side and/or low pressure side pressure difference detection means.

10. The exhaust gas dilution apparatus according to claim 7, further comprising:

result decision means for determining whether the first and second pressure differences obtained by the high pressure side and low pressure side pressure difference detection means, respectively, are within a previously specified range of deviation or above a previously specified correlation coefficient during a period of measurement and outputting a result indicative thereof, or for determining based on the result whether the divider exhibits flow division performance with permissible accuracy.

11. In an exhaust gas dilution apparatus equipped with a divider which divides exhaust gas introduced therein into a plurality of flows and has a first divider pipe for extracting a portion of the gas into a dilution tunnel and a second divider pipe for exhausting a remaining portion of the gas to an exhaust chamber, the exhaust gas dilution apparatus comprising:

first and second flow rate measuring units having equivalent performance, provided in an equivalent position respectively in the first and second divider pipes;

an exhaust adjustment unit adjusting an exhaust from the exhaust chamber; and a control unit controlling the exhaust adjustment unit so that a flow rate of the dilution tunnel measured by the first flow rate measuring unit and a flow rate of the exhaust pipe side measured by the second flow rate measuring unit are equivalent.

12. The exhaust gas dilution apparatus according to claim 11, wherein the second flow rate measuring unit comprises:

dividers, venturis, one provided in each of the dividers, pressure difference detectors measuring a pressure difference between a high pressure side and a low pressure side of each venturi, and an averaging circuit averaging the electric signals detected by the pressure difference detectors.

13. The exhaust gas dilution apparatus according to claim 11, wherein the second flow rate measuring unit comprises:

dividers, venturis for measurement in representative dividers selected from the dividers, and dummy venturis in the plurality of dividers, excluding the dividers for which the venturis for measurement are provided, and have a throttle with the same configuration as that provided in the venturis for measurement.

14. The exhaust gas dilution apparatus according to claim 11, wherein the second flow rate measuring unit comprises:

dividers, pressure introduction pipes, venturis, one provided in each of the dividers, and one pressure difference detector for measuring a pressure difference between a high pressure side and a low pressure side in combined pressure introduction pipes on the high pressure side and the low pressure side, which are formed by respectively combining the pressure introduction pipes of the venturis on the high pressure side and the low pressure side.

15. The exhaust gas dilution apparatus according to claim 11, further comprising:

a monitor unit continuously monitoring the flow rates obtained by the first and/or second flow rate measuring units.

16. The exhaust gas dilution apparatus according to claim 11, further comprising:

a result decision unit determining whether differences in the flow rates obtained by the first and second flow rate measuring units are within a previously specified range of deviation or above a previously specified correlation coefficient during a period of measurement and outputting results indicative thereof, or for determining based on the results, whether the divider exhibits flow division performance with permissible accuracy.

17. In an exhaust gas dilution apparatus equipped with a divider which divides exhaust gas introduced therein into a plurality of flows and has a first divider pipe for extracting a portion of the gas into a dilution tunnel and a second divider pipe for exhausting the remaining portion to an exhaust chamber, the exhaust gas dilution apparatus comprising:

first and second fluid throttling units having equivalent performance, provided in an equivalent position respectively in the first and second divider pipes;

a high pressure side pressure difference detection unit detecting a first pressure difference between a high pressure side of the first fluid throttling unit and a high pressure side of the second fluid throttling unit;

a low pressure side pressure difference detection unit detecting a second pressure difference between a low pressure side of the first fluid throttling unit and a low pressure side of the second fluid throttling unit;

an exhaust adjustment unit adjusting an exhaust from the exhaust chamber; and a control unit controlling the exhaust adjustment unit so that the first and second pressure differences detected are equivalent and zero.

18. The exhaust gas dilution apparatus according to claim 17, wherein the high pressure side pressure difference detection unit and the low pressure side pressure difference detection unit each comprise a cylinder, a free piston slidably inserted into the cylinder, and a piston position detecting unit detecting a position of the free piston.

19. The exhaust gas dilution apparatus according to claim 17, further comprising:

a monitor unit to continuously monitoring the first and/or the second pressure differences obtained by the high pressure side and/or low pressure side pressure difference detection units.

20. The exhaust gas dilution apparatus according to claim 17, further comprising:

a result decision unit determining whether the first and second pressure differences obtained by the high pressure side and low pressure side pressure difference detection units, respectively, are within a previously specified range of deviation or above a previously specified correlation coefficient during a period of measurement and outputting a result indicative thereof, or for determining based on the result whether the divider exhibits flow division performance with permissible accuracy.

* * * * *